(12) United States Patent
Weisbrod

(10) Patent No.: US 6,454,922 B1
(45) Date of Patent: Sep. 24, 2002

(54) CORROSION TEST CELL FOR BIPOLAR PLATES

(75) Inventor: Kirk R. Weisbrod, Los Alamos, NM (US)

(73) Assignee: The Regents of the University of California, Los Alamos, NM (US)

( * ) Notice: Subject to any disclaimer, the term of this patent is extended or adjusted under 35 U.S.C. 154(b) by 75 days.

(21) Appl. No.: 09/602,402

(22) Filed: Jun. 23, 2000

(51) Int. Cl.⁷ ............................................. G01N 27/26
(52) U.S. Cl. .................. 204/404; 204/400; 429/30; 429/33
(58) Field of Search ................... 204/400, 404, 204/434, 237, 239, 269, 270, 274

(56) References Cited

U.S. PATENT DOCUMENTS

| | | | |
|---|---|---|---|
| 3,449,232 A | * | 6/1969 | Bailey |
| 3,737,379 A | * | 6/1973 | Tosteson |
| 3,839,180 A | * | 10/1974 | Takaysu |
| 4,049,525 A | | 9/1977 | Dutton et al. ................ 204/195 |
| 5,493,904 A | | 2/1996 | Shih et al. ................ 73/150 R |

OTHER PUBLICATIONS

R. L. Borop et al., "Design and Testing Criteria for Bipolar Plate Materials for PEM Fuel Cell Applications," Mat. Res. Soc. Symp. Proc., vol. 393, (1995) Month unavailable.

L. Ma et al., "Evaluation of Materials for Bipolar Plates in PEMFCs," Proc. Symp. New Materials for Electrochemical Systems (1999) Month unavailable.

* cited by examiner

Primary Examiner—T. Tung
(74) Attorney, Agent, or Firm—Samuel L. Borkowsky

(57) ABSTRACT

A corrosion test cell for evaluating corrosion resistance in fuel cell bipolar plates is described. The cell has a transparent or translucent cell body having a pair of identical cell body members that seal against opposite sides of a bipolar plate. The cell includes an anode chamber and an cathode chamber, each on opposite sides of the plate. Each chamber contains a pair of mesh platinum current collectors and a catalyst layer pressed between current collectors and the plate. Each chamber is filled with an electrolyte solution that is replenished with fluid from a much larger electrolyte reservoir. The cell includes gas inlets to each chamber for hydrogen gas and air. As the gases flow into a chamber, they pass along the platinum mesh, through the catalyst layer, and to the bipolar plate. The gas exits the chamber through passageways that provide fluid communication between the anode and cathode chambers and the reservoir, and exits the test cell through an exit port in the reservoir. The flow of gas into the cell produces a constant flow of fresh electrolyte into each chamber. Openings in each cell body is member allow electrodes to enter the cell body and contact the electrolyte in the reservoir therein. During operation, while hydrogen gas is passed into one chamber and air into the other chamber, the cell resistance is measured, which is used to evaluate the corrosion properties of the bipolar plate.

19 Claims, 9 Drawing Sheets

CORROSION TEST CELL FOR BIPOLAR PLATES

FIELD OF THE INVENTION

The present invention relates generally to electrochemical cells and more particularly to a corrosion test cell for bipolar plates used in electrochemical cells such as fuel cells. This invention was made with government support under Contract No. W-7405-ENG-36 awarded by the U.S. Department of Energy to the contract to the University of California. The U. S. Government has certain rights in the invention.

BACKGROUND OF THE INVENTION

A continuing desire to reduce dependency on petroleum as an energy source and to reduce fuel emissions has provoked intense interest in fuel cells as alternative energy sources. Briefly, a fuel cell produces electricity generated from the oxidation of hydrogen, the fuel of the cell. Fuel cells include an anode through which hydrogen gas is passed. The hydrogen is oxidized to hydrogen ions, and electrons from the oxidation are delivered via an external circuit to the cell cathode where they combine with oxygen to produce oxygen anions. Hydrogen ions generated in the anode chamber flow through a proton exchange membrane (PEM) to the to the cathode chamber where they combine with the oxygen anions to produce water.

In order to obtain usable voltages for various applications, a stack of about 100–200 cells in series is generally, required. These cell stacks require bipolar plates, which perform several functions: they allow the conduction of electrons between fuel cells with minimal electrical resistance; they prevent the transfer of materials between fuel cells; they also provide a flow structure for gas distribution in a fuel cell. Importantly, fuel cells form corrosive solutions with which bipolar plates are in constant contact. Any corrosion products resulting from contact would contaminate the PEM and increase the internal resistance of the cell and decrease the cell lifetime. Therefore, bipolar plates should be highly corrosion resistant. In addition, bipolar plates contribute a significant fraction of the cost of a fuel cell, and the development of low cost bipolar plates and those materials used to produce them is a significant challenge for commercialization of PEM fuel cells.

The corrosion properties of materials can be tested using a corrosion test cell. One such cell has been described in U. S. Pat. No. 4,049,525 to D. R. Dutton and T. C. Musolf entitled "Corrosion Test Cell", which issued Sep. 20, 1977. This cell tests metal rods for corrosion, and can test several simultaneously. This test cell includes an electrically nonconductive vessel, a corrosive electrolyte solution in the vessel, and reference and auxiliary electrodes immersed in the solution. One end of each rod is attached to an electrode that is immersed in the electrolyte solution. The other end of the rod is outside the vessel, and is attached to a device that records the potentiodymanic anodic polarization curve for that particular rod. The middle of the rod is insulated from the solution with Teflon™.

A paper to R. L. Borop and N. E. Vanderborgh entitled "Design and Testing Criteria for Bipolar Plate Materials for PEM Fuel Cell Applications", which appeared in Mat. Res. Soc. Symp. Proc. Vol. 393, (1995), suggests various materials that could be useful for bipolar plates.

A paper by L. Ma, S. Warthesen, and D. A. Shores entitled "Evaluation of Materials for Bipolar Plates in PEMFCs", in Proc. Symp. On New Materials for Electrochemical Systems (1999) evaluates the performance of several corrosion resistant alloys for bipolar plates.

The practical development of fuel cells includes the development of optimal bipolar plate materials. Corrosion test cell for evaluating the corrosion properties of bipolar plate materials is therefore highly desirable. Therefore, an object of the present invention is to provide a corrosion test cell for testing the performance of bipolar plates.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention as embodied and broadly described herein, the present invention includes a corrosion test cell for evaluating corrosion resistance in fuel cell bipolar plates is described. The cell has a transparent or translucent cell body having a pair of identical cell body members that seal against opposite sides of a bipolar plate. The cell includes an anode chamber and a cathode chamber, each on opposite sides of the plate. Each chamber contains a pair of mesh platinum current collectors and a catalyst layer pressed between current collectors and the plate. Each chamber is filled with an electrolyte solution that is replenished with fluid from a much larger electrolyte reservoir. The cell includes gas inlets to each chamber for hydrogen gas and air. As the gases flow into a chamber, they pass along the platinum mesh, through the catalyst layer, and to the bipolar plate. The gas exits the chamber through passageways that provide fluid communication between the anode and cathode chambers and the reservoir, and exits the test cell through an exit port in the reservoir. The flow of gas into the cell produces a constant flow of fresh electrolyte into each chamber. Openings in each cell body member allow reference electrodes to enter the cell body and contact the electrolyte in the reservoir therein. During operation, while hydrogen gas is passed into one chamber and air into the other chamber, the cell resistance is measured, which is used to evaluate the corrosion properties of the bipolar plate.

BRIEF DESCRIPTION OF THE DRAWINGS

The accompanying drawings, which are incorporated in and form a part of the specification, illustrate embodiments of the present invention and, together with the description, serve to explain the principles of the invention.

In the Figures.

DETAILED DESCRIPTION OF THE INVENTION

Briefly, the invention includes a corrosion test cell that is used to evaluate the corrosion properties of bipolar plate materials. The cell has a pair of cylindrical non-conducting transparent or translucent cell body members that seal against opposite sides of a bipolar plate. The invention allows both sides of the bipolar plate, the side in contact with the anode and the side in contact with the cathode, to be evaluated for corrosion in parallel. The test cell has an anode chamber and a cathode chamber, the plate separating the anode chamber from the cathode chamber. Each chamber contains a pair of mesh platinum current collectors and a catalyst layer pressed between current collectors and the plate. Each chamber is filled with an electrolyte solution that is continuously replenished with fluid from an electrolyte reservoir. The cell includes gas inlets to each chamber, one for fuel (hydrogen), the other for oxidant gas (air, oxygen). As each gas flows into its respective chamber, it flows along the platinum mesh, through the catalyst layer, and to the bipolar plate. The gas exits the chamber through passageways between the chamber and the reservoir and exits the test cell through an exit port in the cell body. Thus, the movement of gas into and out of the chamber also produces the flow of electrolyte from the reservoir to the chamber and from the chamber to the reservoir. Openings in each cell body member allow reference electrodes to enter the cell body and contact the electrolyte in the reservoir. During operation, hydrogen gas is passed into one chamber and air into the other chamber and the cell resistance is measured. An increase in cell resistance over time is one indication that corrosion is taking place. After a test run, the bipolar plate is removed and both sides are examined for corrosion. Electrolyte from each reservoir may also be analyzed for corrosion products. This way, the corrosion properties of the plate and therefore of the materials used to make the plate can be evaluated. Reference will now be made in detail to the present preferred embodiments of the invention. Similar or identical structure is identified using identical callouts.

Figure 1:
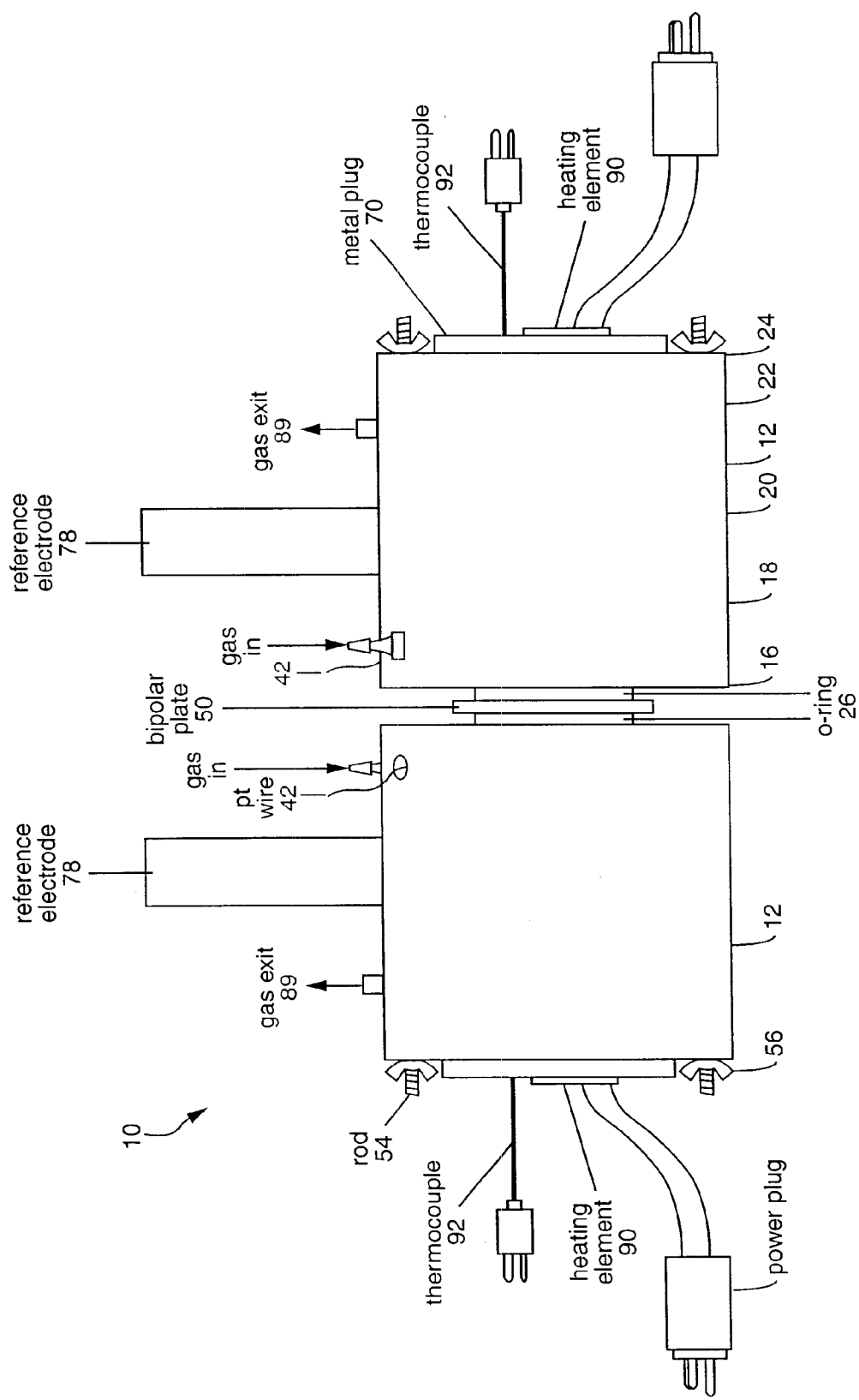
FIG. 1 is a perspective view of the invention.
Figure 2:
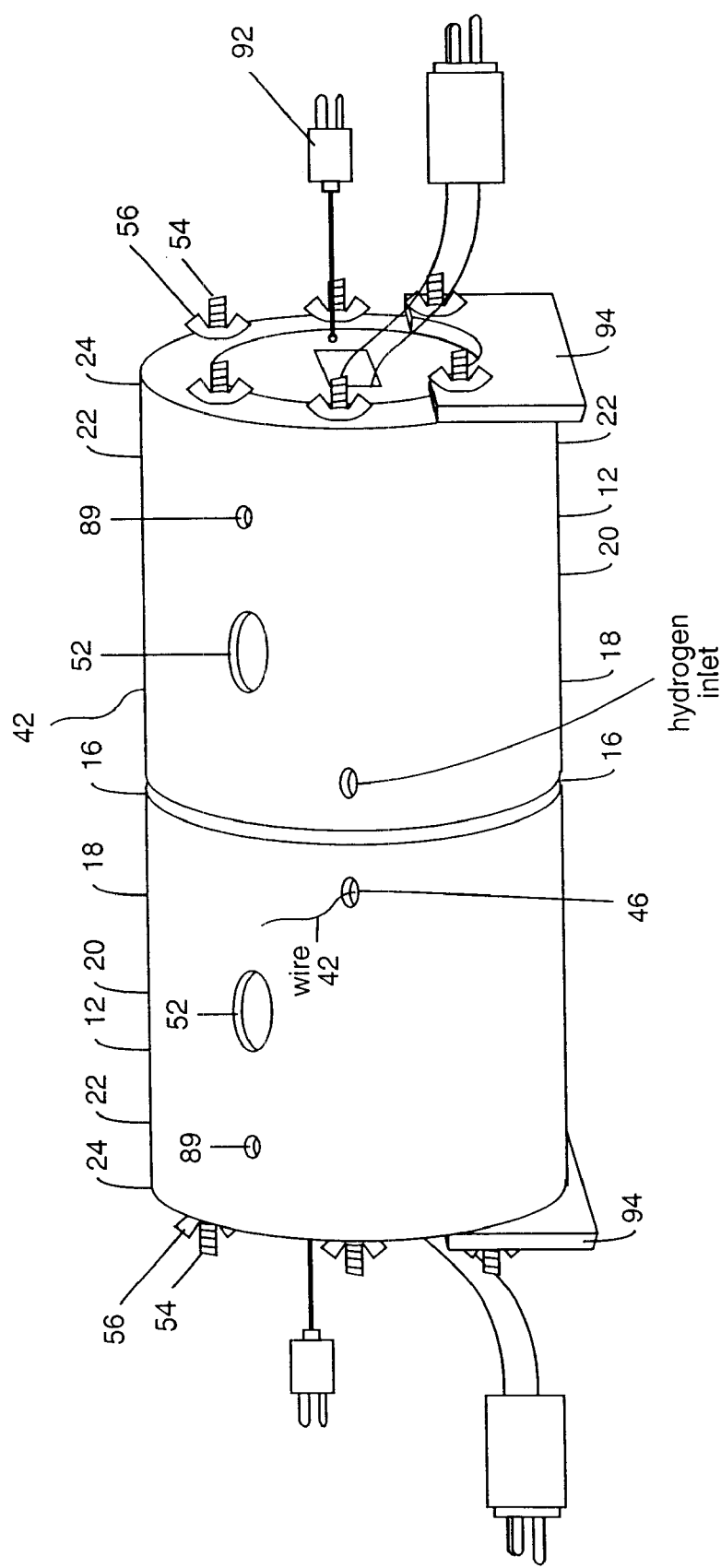
FIG. 2 is a perspective side view of the invention.

A perspective side view of an assembled cell is shown in FIG. 1, and a perspective side view is shown in FIG. 2 with some parts omitted so that aspects of the cell can be viewed more clearly. FIGS. 1 and 2 show cell 10, which includes two cylindrical cell body members 12.

Figure 3:
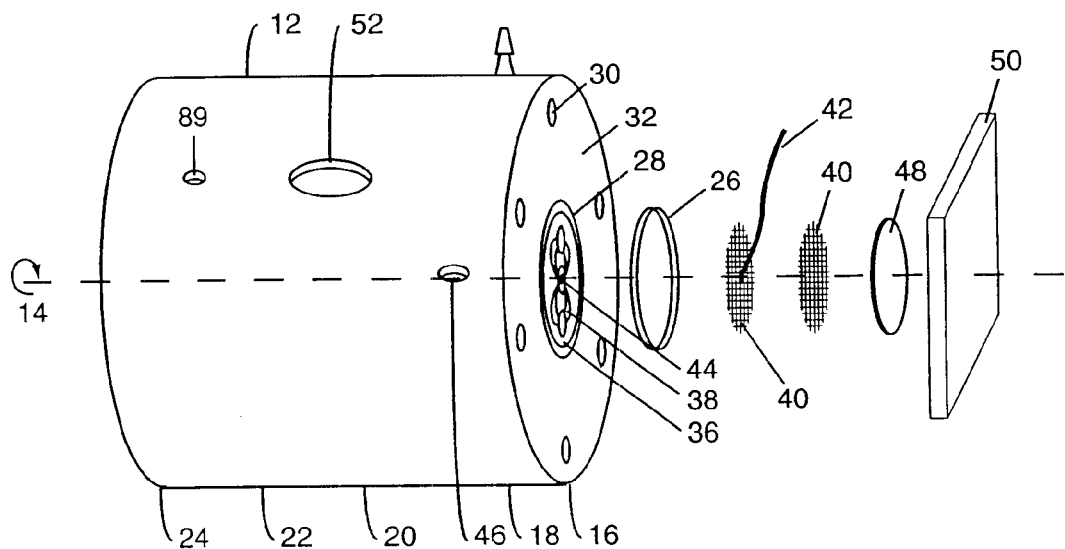
FIG. 3 is a perspective top and side view of a cell body member.
Figure 4:
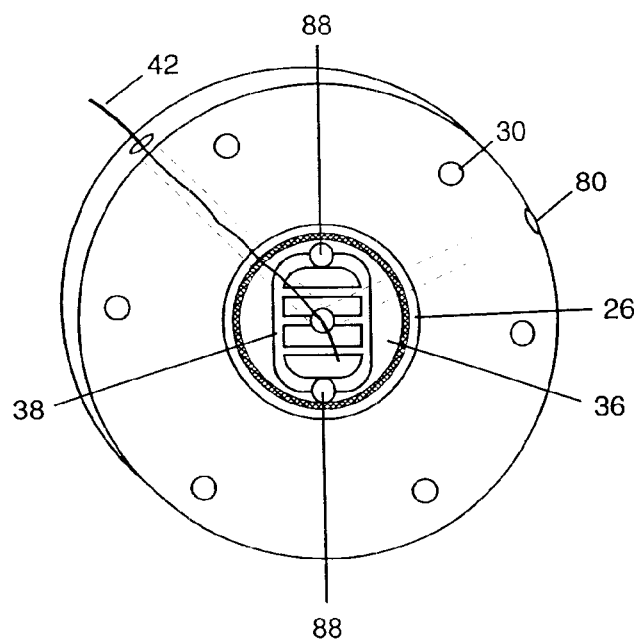
FIG. 4 is a perspective end view from one side of the cell body member of the invention.

FIG. 3 shows an exploded and slanted perspective view showing the side, top, and one end of cell body member 12, and some of the other parts of the cell. FIG. 4 shows an end view looking inward from first end 16. As shown in FIG. 3, cell body member 12 is made from a light, strong, corrosion resistant material such as polyurethane or polycarbonate, preferably transparent or translucent. Cell body member 12 has an axis 14 and includes a first end 16, a first end portion 18, a middle portion 20, a second end portion 22, and a second end 24. A first sealing o-ring 26 is placed within an annular recess 28, coaxial with body axis 14, in second end 22. O-ring 26 is compressible, corrosion resistant, and solvent resistant, preferably a material such as Viton or other fluorinated polymer. FIG. 3 shows six equally spaced longitudinal rod passageways 30 in the cell body outer wall 32. FIG. 3 also shows a circular recess 36 in first end 16 of body member 12, having a recess surface including indentations defining a fluid flow field 38, more clearly seen in FIG. 4. The anode/cathode and corresponding anode chamber/cathode chamber result as follows. A first platinum current collector 40 is spot welded to wire 42. Wire 42 then is passes through opening 44 centered within recess 36 and through a passageway leading to opening 46 until current collector 40 is within recess 36 and flush against flow field 38. Then, a second current collector 40 is positioned against the first current collector, and then a catalyst layer 48. The catalyst used was a commercially available ELAT catalyst including platinum on carbon paper. Then, the bipolar plate 50 to be tested is positioned over sealing o-ring 26 and secured with tape. Similarly, current collectors 40 and catalyst layer 48 are positioned within the recess of a second, identical body member 12. The next step is more easily seen using FIG. 1 and FIG. 2. The first end 16 of the second body member is positioned on the opposite side of bipolar plate 50 so that the body members are coaxial. Body members 12 are rotated until all of the rod passageways 30 are aligned and reference cell inlets 52 for receiving reference electrodes 40 are parallel. Threaded rods 54 are then inserted into rod passageways 30, and wing nuts 56 are screwed onto the ends of these rods to compress O-rings 26 of each body member 12 against opposite sides of bipolar plate 50. Six rods allow an evenly distributed compression against the bipolar plate. Using rods to compress is clearly only one of many strategies that can be used to achieve the same effect.

Figure 5:
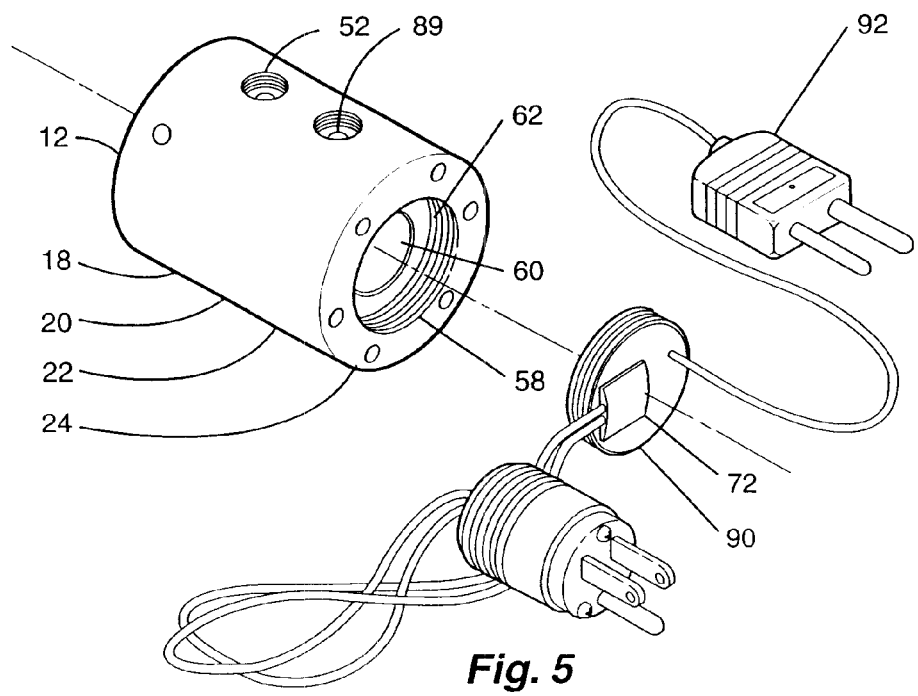
FIG. 5 is another perspective top and side end view from the other side of the cell body member of the invention.
Figure 6:
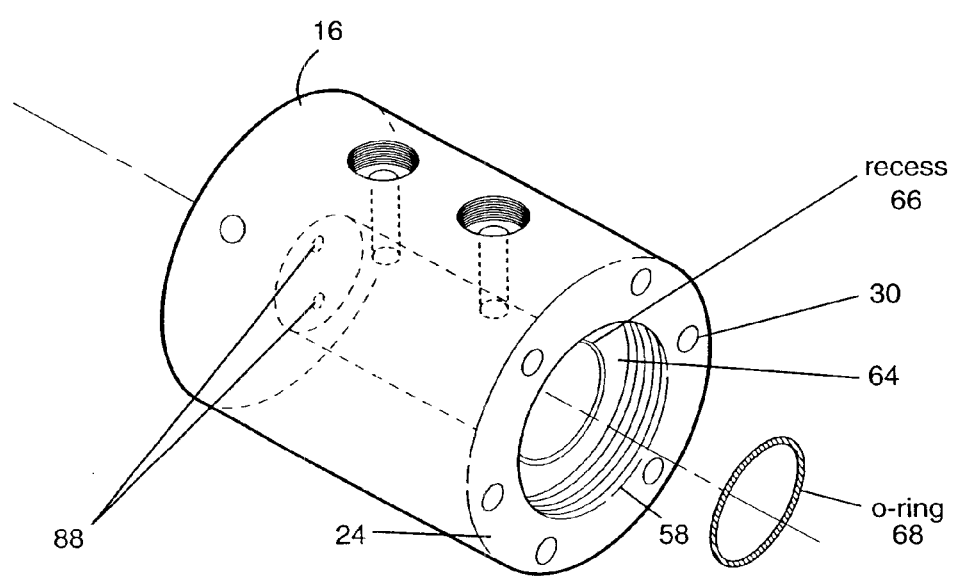
FIG. 6 is an isometric projection view of the cell body member.

With some of the cell now assembled, we turn to FIGS. 5 and 6. FIG. 5 shows an exploded perspective slanted view of some of the top, the side, and second end 24 of cell body member 12. FIG. 6 shows an isometric projection view looking inside cell body member 12 through cylindrical opening 58. Opening 58 leads first to first hollow volume 60 in second end portion 22 of body member 12. Inner threaded surface 62 (more easily seen in FIG. 5) and an annular surface 64 (more easily seen in FIG. 6) defines first hollow volume 60. Annular surface 64 is perpendicular to threaded surface 62. Annular surface 64 includes recess 66 into which is placed a second sealing o-ring 68. The corrosion test cell also includes cylindrical plug 70, which has an outer threaded surface configured for threaded engagement within first hollow volume 60. Plug is screwed into cell body 12 until plug sealing surface 72 compresses and forms a seal with o-ring 68, which is most clearly seen in the cross-sectional view shown in FIG. 7. Sealing surface 72 is a non-conducting, corrosion resistant, polymeric coating such as a Teflon™ coating.

Figure 7:
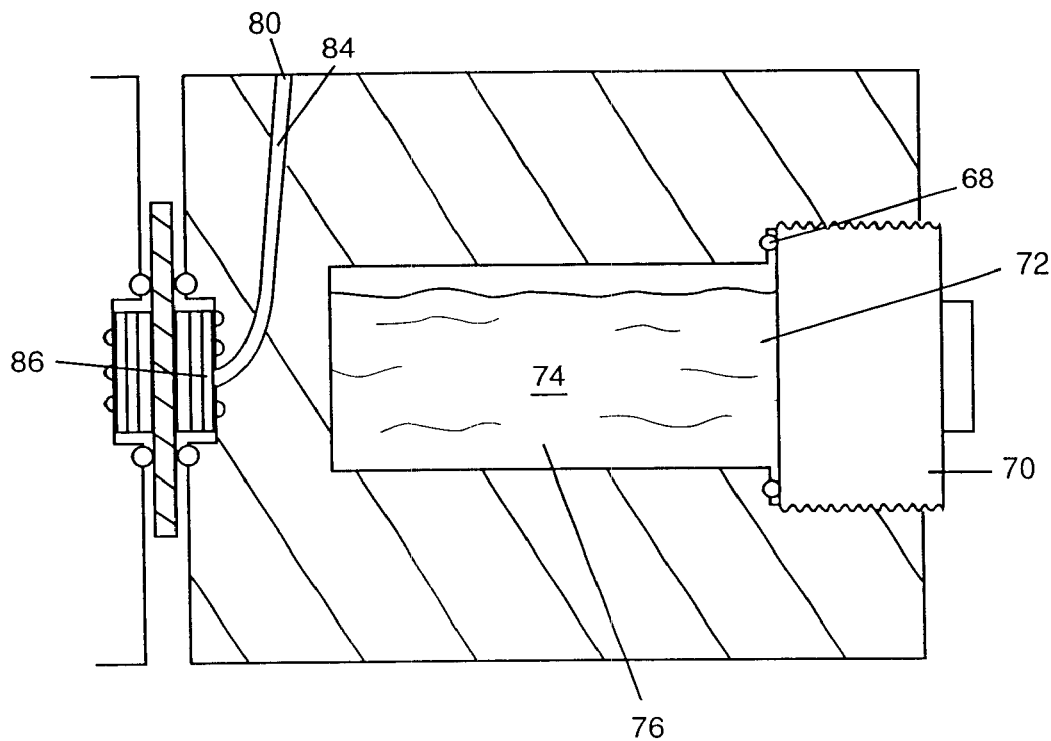
FIGS. 7–8 are cross-sectional views of the cell body member and plug of the invention.

With both first end 16 and second end 24 sealed, electrolyte reservoir chamber 74 is created inside cell body member 12, as shown in FIG. 7. Electrolyte solution 76 is placed into the chamber. The electrolyte solution used was a dilute aqueous sulfuric acid solution with dissolved fluoride anion, and was meant to simulate the behavior of a proton exchange membrane, such as a Nafion membrane, that is typically used with electrochemical cells such as fuel cells or chlor alkali cells. After adding the electrolyte solution 76, a reference electrode 78 is inserted into the reference electrode inlet 52 each body member 12. The reference electrodes are connected to a pH meter or other similar device where reference electrodes are used to measure the pH of the electrolyte solution. Reference electrodes are present in both the anode and cathode reservoirs to measure the electrochemical potential between the metal components and solution. This measurement confirms that the bipolar plate is exposed to the same electrochemical potential as a bipolar plate in a fuel cell. The potential represents the difference in potential between the reference electrode and the Pt electrode in contact is with either hydrogen or air. In some cases, corrosion of the bipolar plate may lead to a mixed potential.

Oxidant gas is then introduced into gas inlet 80, and fuel gas, hydrogen, is introduced into gas inlet 82. FIG. 7 shows inlet 80 and passageway 84 through which gas flows and enters the cathode chamber 86. FIG. 4 shows that gas enters the anode/cathode chamber through the same opening in recess 36 of first end 16 that wire 42 passes through, which is shown in FIG. 4.

Figure 8:
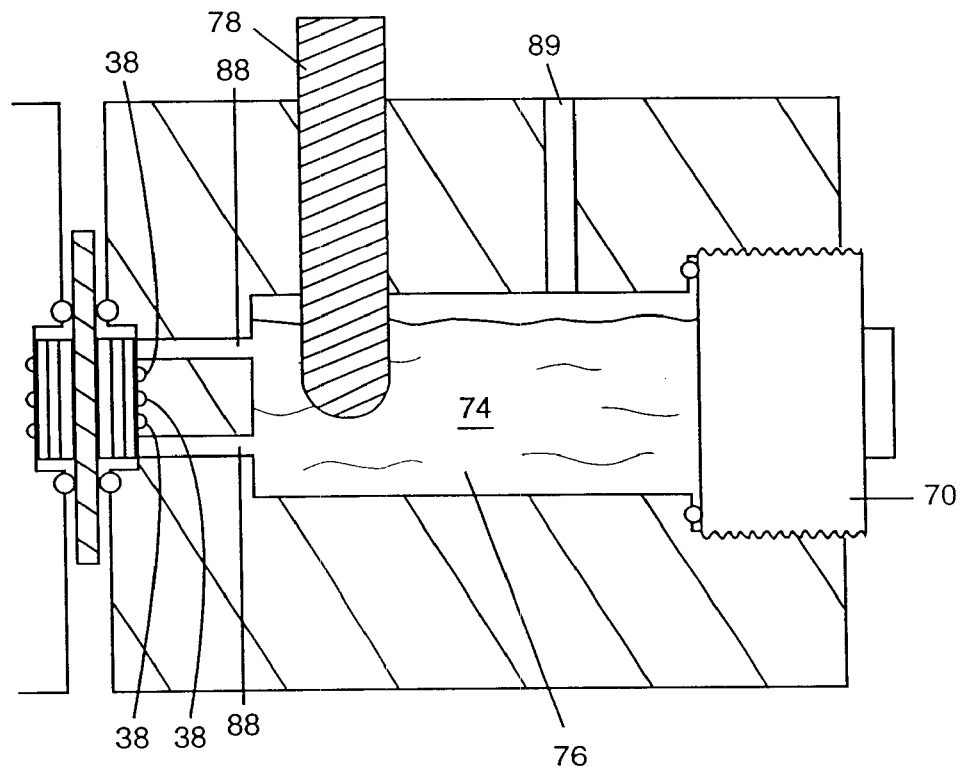

FIG. 8 shows a cross-sectional view of cell body member rotated 60 degrees along body axis 14 relative to FIG. 7. As FIG. 8 shows, electrolyte 74 enters cathode chamber 86 via passageways 88. Gas also exits cathode chamber 86 via passageways 88 and as it flows out of the cathode chamber, it promotes the flow of fresh electrolyte from reservoir chamber 74 and into cathode chamber 88. Gas exits the cell body via gas exit 89. This way, gas pressure does not build up in the cell.

Corrosion test cell 10 was heated to a desired temperature using heating element 90. The plug is in contact with the electrolyte solution and as it is heated, it heats the electrolyte solution. Thermocouple device 92 in contact with plug was used as part of a temperature control device to measure the temperature of plug 70.

As shown in FIG. 2, cell body 10 was stabilized by mounting a base member 94 through two bottom rods to one end of cell 10, and mounting a second base member 94 through the other ends of the same rods to the other end of cell 10. The cell is now sealed, filled with electrolyte, and ready for reactant gases. Cell 10 performs best with a low gas flow rate, several bubbles of gas per minute, which was metered in using a gas metering device.

We now turn to examples of bipolar plates whose corrosion properties were evaluated using the present invention. Briefly, corrosion test cell results were obtained for bipolar plates made of aluminum, 316 stanless steel, titanium and Hastelloy C276.

Figure 9:
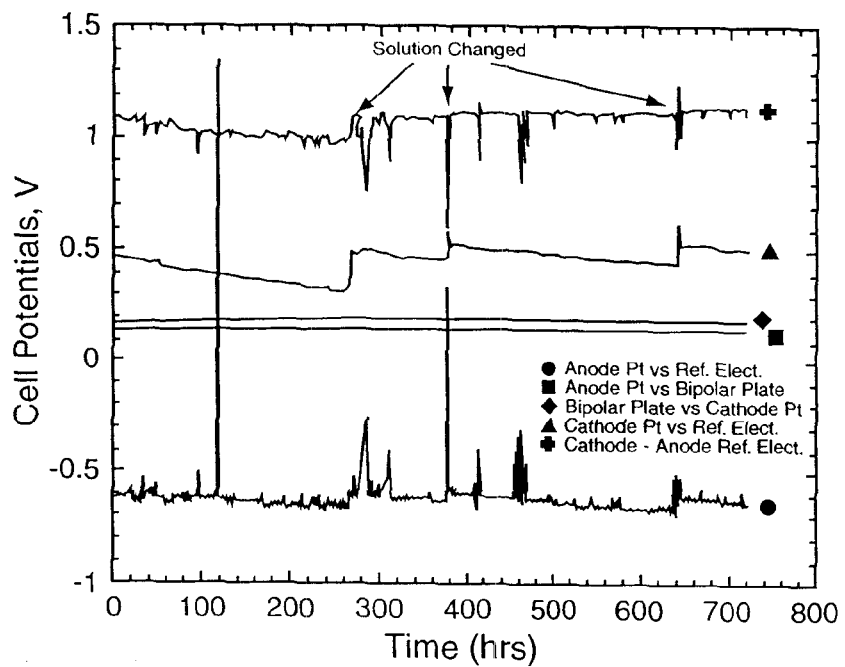
FIG. 9 is a graphical representation of cell potential vs. time for the cell potential transients for a stainless steel bipolar plate.

FIG. 9 shows a graph of cell potential in volts versus time in hr for the cell potential transients recorded for a bipolar plate made of 316 stainless steel. Reference electrode potentials indicated that the bipolar plate was exposed to conditions similar to those within an operating fuel cell. Changes in pH with time are reflected by the reference potential. High dissolution rates for aluminum led to high contact resistance and soluble ion concentrations. The stainless steel bipolar plate experienced intermediate performance and would be accepable for shorter term applications. The electrolyte solution was a N $H_2SO_4$ solution with 2 ppm fluoride anion ($F^{31}$) at a temperature of about 80° C. Hydrogen gas at 1 atmosphere pressure at the anode and air at 1 atmosphere pressure was used at the cathode. The graph shows five curves. There are, from the top to the bottom: a curve of anode potential vs. reference electrode potential; anode potential vs. bipolar plate potential; bipolar plate potential vs. cathode potential; cathode potential vs. reference electrode potential; and cathode vs. anode potential as measured by reference electrodes. Current density through the bipolar plate was 1 amp/cm² in all bipolar plates used.

Figure 10:
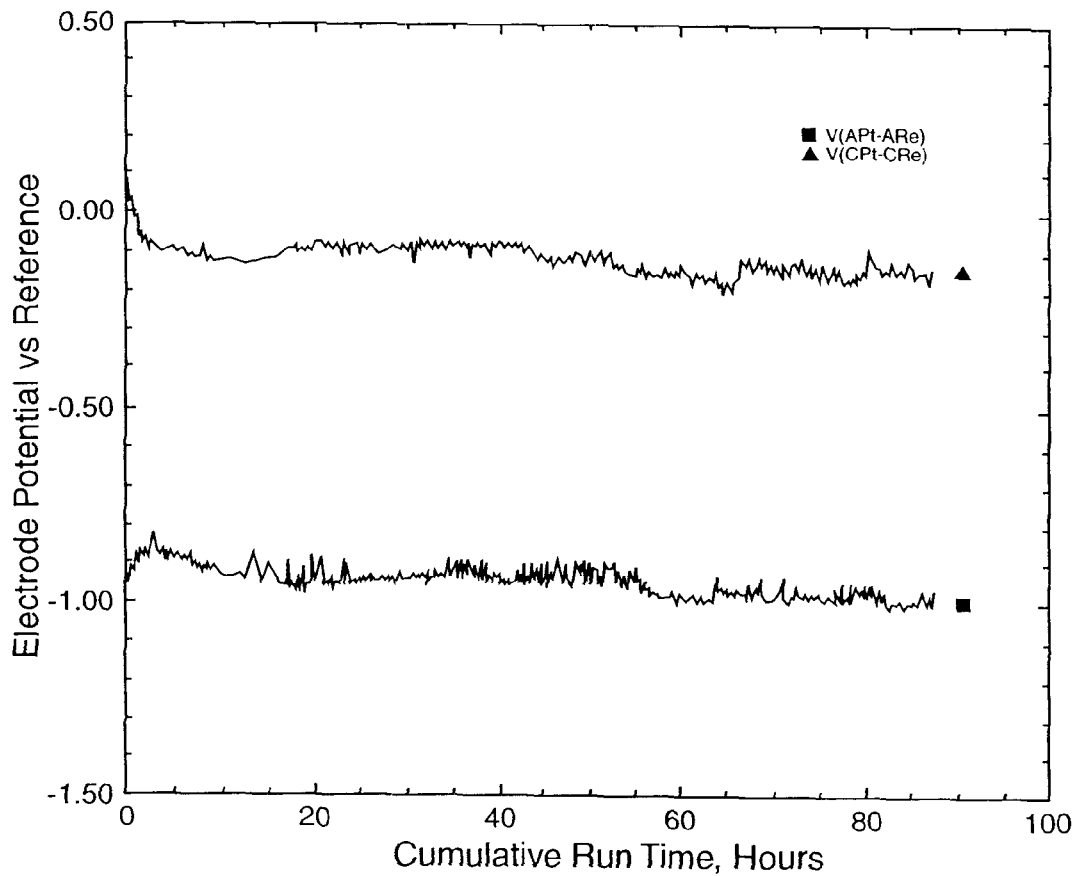
FIG. 10 is a graphical representation of electrode potential vs time for an aluminum bipolar plate.
Figure 11:
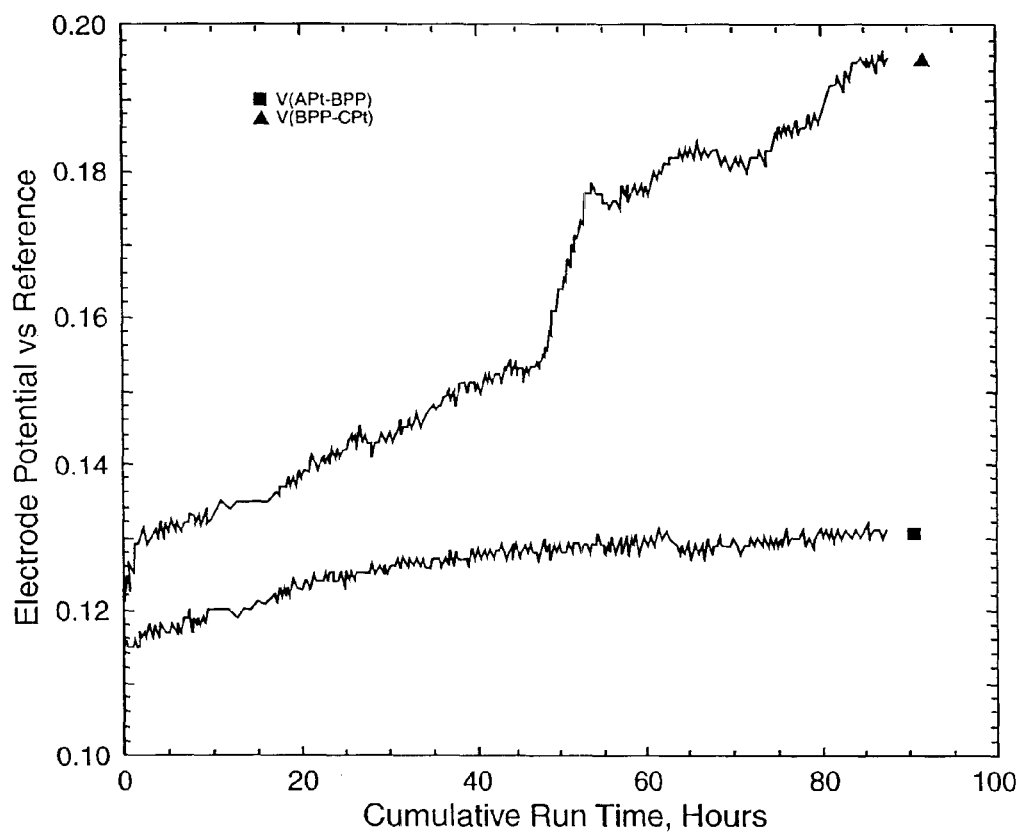
FIG. 11 shows a graphical representation of measured potential drop vs time for aluminum bipolar plate.

A pure aluminum sample shows rapid failure. FIG. 10 shows a graphical representation of, on the y-axis, the measured electrode potential, which was measured versus the reference potential, and on the x-axis, the cumulative run time in hours. The measured potentials indicate that each side of the aluminum bipolar plate was exposed to electrochemical potentials expected in a fuel cell. We also observe that the reference potentials dropped as solution pH decreases. Resistance across the aluminum bipolar plate increased in a striking manner in less than a week, as shown in FIG. 11, the potential rise across the bipolar plate interfaces versus run time for an aluminum electrode. Cathode resistance has increased by nearly 80 mv while the anode increased 14 mv.

After a test of up to 1000 hours, the electrolyte samples can be analyzed to determine the quantity of metal dissolved from the bipolar plate. Assuming a given capture efficiency, the life of the membrane may be estimated.

Figure 12:
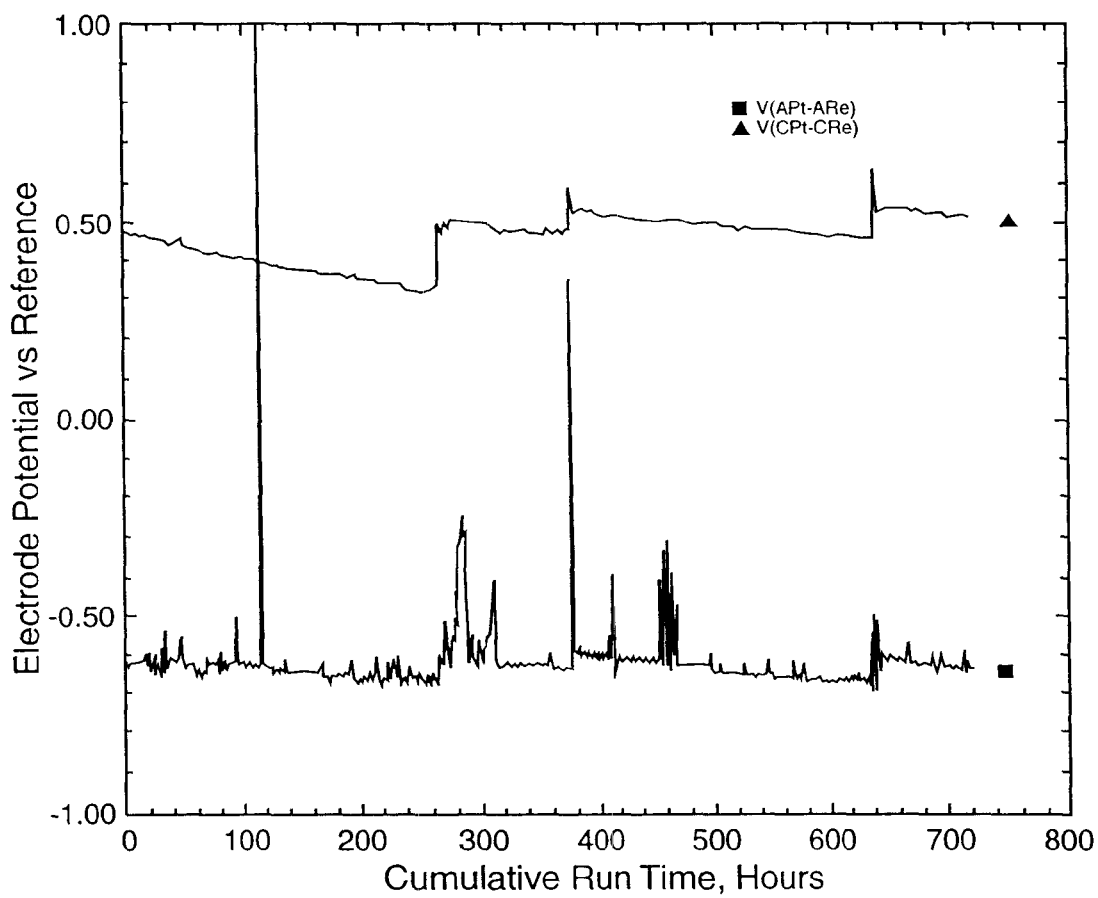
FIG. 12 shows a graphical representation of anode and cathode electrode potentials vs. reference electrode potentials for a stainless steel bipolar plate.

FIG. 12 shows a graphical representation of Anode and cathode electrode potentials versus reference electrode potentials for a 316 SS electrode for 700 hours of operation. As FIG. 12 shows, the total potential difference between the reference electrodes remained nearly constant at 1 volt. This value is slightly higher that a fuel cell open curcuit voltage because there is no hydrogen crossover which depolarizes the cathode. The voltage of both the anode and cathode reactions is dependent upon hydrogen ion concentration (solution pH) as shown in the following reactions:

$$H_2 \rightarrow 2H^+ + 2e^- \tag{1}$$

$$\frac{1}{2}O_2 + 2H^+ + 2e^- \rightarrow H_2O \tag{2}$$

During the week, the pH of the electrolyte changed from an initial value of 3 to an average of 3.8 at the anode and 4.5 at the cathode. This change is reflected by the movement in the negative direction of the potential versus the reference electrodes. Electrolytes were exchanged with fresh solution at the positive jumps in cathode potential.

Figure 13:
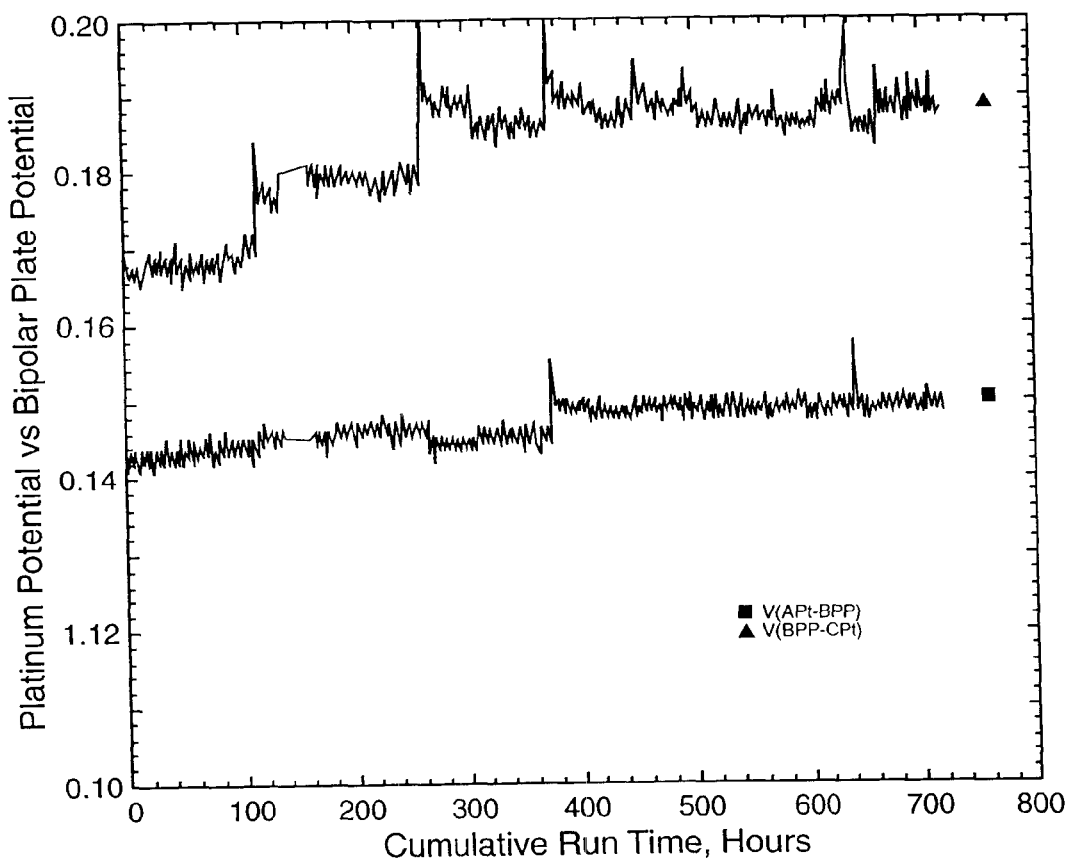
FIG. 13 shows a graphical representation of the rise in potential across the interfaces of a stainless steel bipolar plate vs. time.

FIG. 13 shows a graphical representation of the rise in potential across the interfaces of a stainless steel bipolar plate versus time. The potential between the platinum screens and bipolar plate is given for both the anode and cathode. During the 700 hour test, the resistance between the platinum components and the bipolar plate increased by 20 mv at the cathode and about 7 mv at the anode. Much of the increase appeared to occur when the old electrolyte was exchanged for new solution while the cell was at temperature. It appears that this step may have aided in dehydrating the oxidation product. While this step is representative of what would occur in a fuel cell, it may also explain how good performance was initially seen with 316 SS components where cell operation was continuous.

The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A corrosion test cell for testing a bipolar plate, comprising:

(a) an anode and an anode current collector in electrical communication with said anode;

(b) an anode chamber containing said anode and anode current collector;

(c) a cathode and a cathode current collector in electrical communication with said cathode;

(d) a cathode chamber containing said cathode and cathode current collector;

(e) electrolyte solution comprising an aqueous acid;

(f) an anode electrolyte solution reservoir chamber for receiving said electrolyte solution and in fluid communication with said anode chamber;

(g) a cathode electrolyte solution reservoir chamber for receiving said electrolyte solution and in fluid communication with said cathode chamber;

(h) a first reference electrode at least partially submerged into the anode reservoir solution;

(i) a second reference electrode at least partially submerged into the cathode reservoir solution;

(j) means for introducing reducing gas into the anode chamber and for removing it from the test cell;

(k) means for introducing oxidizing gas into the cathode chamber and for removing it from the test cell;

(l) means for circulating electrolyte solution from said anode electrolyte solution reservoir into said anode chamber and from said anode chamber into said anode electrolyte solution reservoir;

(m) means for circulating electrolyte solution from said cathode electrolyte solution reservoir into said cathode chamber and from said cathode chamber into said cathode electrolyte solution reservoir; and (n) a bipolar plate to be tested, said plate having a first surface in contact with said electrolyte solution and said reducing gas, said plate having a second surface in contact with said electrolyte solution and said oxidizing gas.

2. The corrosion test cell of claim 1, wherein said anode comprises a metal catalyst supported on carbon.

3. The corrosion test cell of claim 2, wherein said anode catalyst comprises platinum.

4. The corrosion test cell of claim 1, wherein said cathode comprises a metal catalyst supported on carbon.

5. The corrosion test cell of claim 4, wherein said cathode comprises a platinum catalyst.

6. The corrosion test cell of claim 1, further comprising a power source that supplies power to said test cell.

7. The corrosion test cell of claim 1, further comprising means controlling the temperature of said test cell.

8. The corrosion test cell of claim 1, wherein said electrolyte solution comprises fluoride anion.

9. The corrosion test cell of claim 1, further comprising means for measuring the electrical resistance between the anode and the bipolar plate, the electrical resistance between the cathode and the bipolar plate, and the electrical resistance of the test cell.

10. A corrosion test cell for testing a bipolar plate, comprising:

(a) an anode and an anode current collector in electrical communication with said anode;

(b) a cathode and a cathode current collector in electrical communication with said cathode;

(c) a cylindrical plug comprising a metal body having a first end coated with an electrically resistant and corrosion resistant polymer, a second end parallel to said first end, a middle, and a threaded outer surface;

(d) temperature control means connected to the non-coated end of said plug for heating the plug to a desired temperature;

(e) a first sealing member;

(f) a second sealing member;

(g) electrolyte solution;

(h) a cell body comprising a first cylindrical cell body member comprising a longitudinal axis and a first end, a first end portion, a middle portion, a second end portion, and a second end, said body member having an opening at said first end extending into a first cylindrical hollow volume coaxial within said body member and defined by an inner threaded surface and an annular surface perpendicular to the threaded surface, the threaded surface configured for engagement with the plug, the annular surface including a first annular recess for receiving said first sealing member which seals against the coated surface of the plug;

(i) said first cylindrical cell body member further comprising a second cylindrical hollow portion coaxial with the body axis and extending inward through said middle portion;

(j) said first cylindrical cell body member having a second annular recess at said second end for receiving said second sealing member for sealing said body member with the bipolar plate;

(k) said first cylindrical cell body member having a cylindrical recess at said second end for receiving said anode and said anode current collector and including at least two passageways for fluid flow between said cylindrical recess and said second cylindrical hollow portion;

(l) said first cylindrical cell body member having an opening to said middle portion for receiving a reference electrode;

(m) said first cylindrical cell body member having a gas inlet;

(n) a second cylindrical cell body member identical to said first cylindrical cell body member, wherein the cylindrical recess at the second end of said second cylindrical cell body member receives said cathode and said cathode current collector; and (o) sealing members for said second cylindrical body member that are identical to said first sealing member and said second sealing member.

11. The corrosion test cell of claim 10, wherein said anode comprises a metal catalyst supported on carbon.

12. The corrosion test cell of claim 11, wherein said anode catalyst comprises platinum.

13. The corrosion test cell of claim 10, wherein said cathode comprises a metal catalyst supported on carbon.

14. The corrosion test cell of claim 13, wherein said cathode comprises a platinum catalyst.

15. The corrosion test cell of claim 10, further comprising a power source that supplies power to said test cell.

16. The corrosion test cell of claim 10, wherein said electrolyte solution comprises fluoride anion.

17. The corrosion test cell of claim 10, wherein said cylindrical recess at the second end of said cell body is further defined by a plurality of surface indentations defining a fluid flow field.

18. The corrosion test cell of claim 10, further comprising means for measuring the electrical resistance between the anode and the bipolar plate, the electrical resistance between the cathode and the bipolar plate, and the electrical resistance of the test cell.

19. The corrosion test cell of claim 10, wherein said first body and said second body are non-electrically conducting and corrosion resistant.

* * * * *